(12) United States Patent
Carter et al.

(10) Patent No.: US 11,007,305 B1
(45) Date of Patent: May 18, 2021

(54) BONE GRAFTS WITH CONTROLLED RELEASE CALCIUM

(71) Applicant: THERACELL, INC., Sherman Oaks, CA (US)

(72) Inventors: Andrew J. Carter, Stow, MA (US); Nelson L. Scarborough, Andover, MA (US); Bradley E. Patt, Northridge, CA (US)

(73) Assignee: THERACELL, INC., Sherman Oaks, CA (US)

( * ) Notice: Subject to any disclaimer, the term of this patent is extended or adjusted under 35 U.S.C. 154(b) by 0 days.

(21) Appl. No.: 15/485,221

(22) Filed: Apr. 11, 2017

Related U.S. Application Data

(60) Provisional application No. 62/321,019, filed on Apr. 11, 2016.

(51) Int. Cl.
| | | |
|---|---|---|
| *A61L 27/36* | (2006.01) |
| *A61L 27/46* | (2006.01) |
| *A61L 27/44* | (2006.01) |
| *A61L 27/58* | (2006.01) |
| *A61L 27/18* | (2006.01) |
| *A61L 27/34* | (2006.01) |
| *A61L 27/54* | (2006.01) |

(52) U.S. Cl.
CPC ........... *A61L 27/3608* (2013.01); *A61L 27/18* (2013.01); *A61L 27/34* (2013.01); *A61L 27/446* (2013.01); *A61L 27/46* (2013.01); *A61L 27/54* (2013.01); *A61L 27/58* (2013.01); *A61L 2300/252* (2013.01); *A61L 2300/414* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2007/0255422 A1* | 11/2007 | Wei | A61F 2/28 623/23.51 |
| 2009/0148489 A1* | 6/2009 | Cooper | A61L 27/446 424/423 |
| 2011/0223209 A1* | 9/2011 | Kuijer | A61L 27/04 424/400 |
| 2014/0314822 A1* | 10/2014 | Carter | A61L 27/3608 424/423 |

FOREIGN PATENT DOCUMENTS

WO    WO 2014/151091    *   9/2014

* cited by examiner

*Primary Examiner* — Melissa L Fisher
(74) *Attorney, Agent, or Firm* — Umberg Zipser LLP

(57) ABSTRACT

A bone graft for bone repair, the bone graft having controlled release bone mineral ions includes a resorbable polymer incorporated with a bone mineral ion donor to form a mineral-incorporated resorbable polymer, and demineralized bone matrix (DBM) mixed with the mineral-incorporated resorbable polymer.

6 Claims, 4 Drawing Sheets
(4 of 4 Drawing Sheet(s) Filed in Color)

1  2  3

BONE GRAFTS WITH CONTROLLED RELEASE CALCIUM

CROSS-REFERENCE TO RELATED APPLICATION(S)

The present application claims priority to and the benefit of U.S. Provisional Application Ser. No. 62/321,019 filed on Apr. 11, 2016, entitled "Enhanced Bone Formation Using Bone Grafts Having Controlled Release Calcium," the entire content of which is incorporated herein by reference.

BACKGROUND

Bone grafts are often required to repair skeletal defects due to trauma, deformity, and other conditions including spinal fusion. Autograft from the patient, allograft from donors of the same species and synthetic materials are common options. Allogeneic demineralized bone matrix (DBM) has gained popularity as it has good bone healing characteristics and is readily remodeled by host cells.

No 'ideal' bone graft currently exists. Autograft, often recovered from patients' iliac crest, is often considered the 'gold standard', but involves additional surgical trauma to the patient, time/cost of additional surgical time and supplies, and often results in patient morbidity that is slow to resolve. Quantities of autograft are also limited, and this becomes more problematic in patients with prior bone harvesting procedures. Furthermore, the healing rates, particularly recognized in animal models designed to study bone graft performance, (e.g., rabbit posterolateral spine fusion) have demonstrated less than optimal results, i.e. 70% spine fusion rates.

SUMMARY

In some embodiments of the present invention, a bone graft having controlled release bone mineral ions includes a resorbable polymer incorporated with a bone mineral ion donor to form a mineral-incorporated resorbable polymer, and demineralized bone matrix (DBM) mixed with the mineral-incorporated resorbable polymer. In some embodiments, the bone mineral ions of the bone graft are calcium and/or phosphate ions. In some embodiments, the demineralized bone matrix of the bone graft is demineralized bone fiber. In some embodiments, the resorbable polymer is in the form of a particulate and/or a fiber.

In some embodiments of the present invention, the particulate and/or fiber has an outer polymer layer to provide further controlled release. In some embodiments, the bone mineral ion donor of the bone graft is calcium peroxide, calcium ascorbate, calcium sulfate, calcium phosphate, calcium carbonate, calcium chloride, or mixtures thereof. In some embodiments, the bone graft is in the form of putty, strip, cylinder, cone.

In some embodiments of the present invention, the resorbable polymer of the bone graft is one or more of proteins, peptides, silk, collagen, polysaccharides, resorbable polyesters, including resorbable polyesters made from hydroxy acids, resorbable polyesters made from diols and diacids; polycarbonates; tyrosine polycarbonates, natural and synthetic polyamides, natural and synthetic polypeptides, natural and synthetic polyaminoacids, polyesteramides, poly (alkylene alkylates), polyethers, polyvinyl pyrrolidones, polyurethanes, polyetheresters, polyacetals, polycyanoacrylates, poly(oxyethylene)/poly(oxypropylene) copolymers, polyacetals, polyketals, polyphosphates, (phosphorous-containing) polymers, polyphosphoesters, polyalkylene oxalates, polyalkylene succinates, poly(maleic acids), biocompatible copolymers, hydrophilic or water soluble polymers, or combinations thereof.

In some embodiments of the present invention, the resorbable polymer of the bone graft is a protein or peptide including one or more of alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine; the polysaccharides of the resorbable polymer are selected from alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan; the resorbable polyesters are selected from poly (lactides), poly(glycolides), poly(lactide-co-glycolides), poly(lactic acid), poly(glycolic acid), poly(lactic acid-co-glycolic acid), poly(dioxanones), polycaprolactones and polyesters with one or more of the following monomeric units: glycolic, lactic; trimethylene carbonate, p-dioxanone, or ε-caprolactone; the polyethers of the resorbable polymer are selected from polyethylene glycol (PEG) or polyethylene oxide (PEO); and the biocompatible copolymers are selected from polyethylene (PEG) or (PVP) with a block of a different biocompatible or biodegradable polymers selected from the group consisting of poly(lactide), poly(lactide-co-glycolide), polycaprolactone or combinations thereof.

In some embodiments of the present invention, the resorbable polymer includes a structure selected from a fiber, film, foam, sponge, gel, sphere, particle, core-sheath fiber, laminate, or combinations thereof.

In some embodiments of the present invention, the bone graft as disclosed above also includes an excipient selected from glycerols, lecithins, polyoxamers, surfactants, or phospholipids.

In some embodiments of the present invention, the bone mineral ion donor is selected from tricalcium phosphate (TCP), hydroxyapatite (HA), calcium phosphate, or mixtures thereof.

In some embodiments of the present invention, a method of repairing a bone or a bone defect in a subject in need thereof, includes implanting the bone graft having controlled release bone mineral ions includes a resorbable polymer incorporated with a bone mineral ion donor to form a mineral-incorporated resorbable polymer, and demineralized bone matrix (DBM) mixed with the mineral-incorporated resorbable polymer as disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
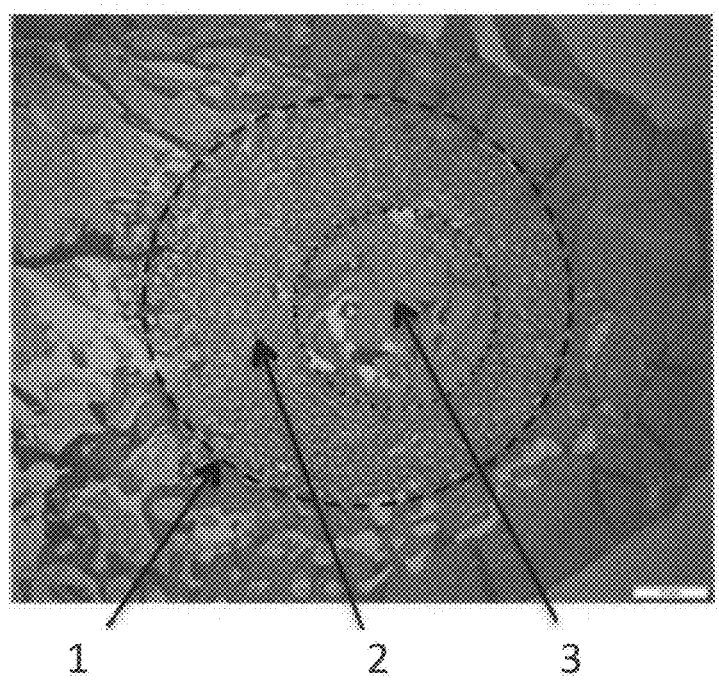
FIG. 1 is a histological section from a rabbit femoral condyle 6 mm diameter by 10 mm deep defect treated with demineralized bone fibers (DBF) for two weeks, according to embodiments of the present invention, in which (1) indicates the outline of the defect, (2) indicates the new woven bone and (3) indicates residual DBF.
Figure 2:
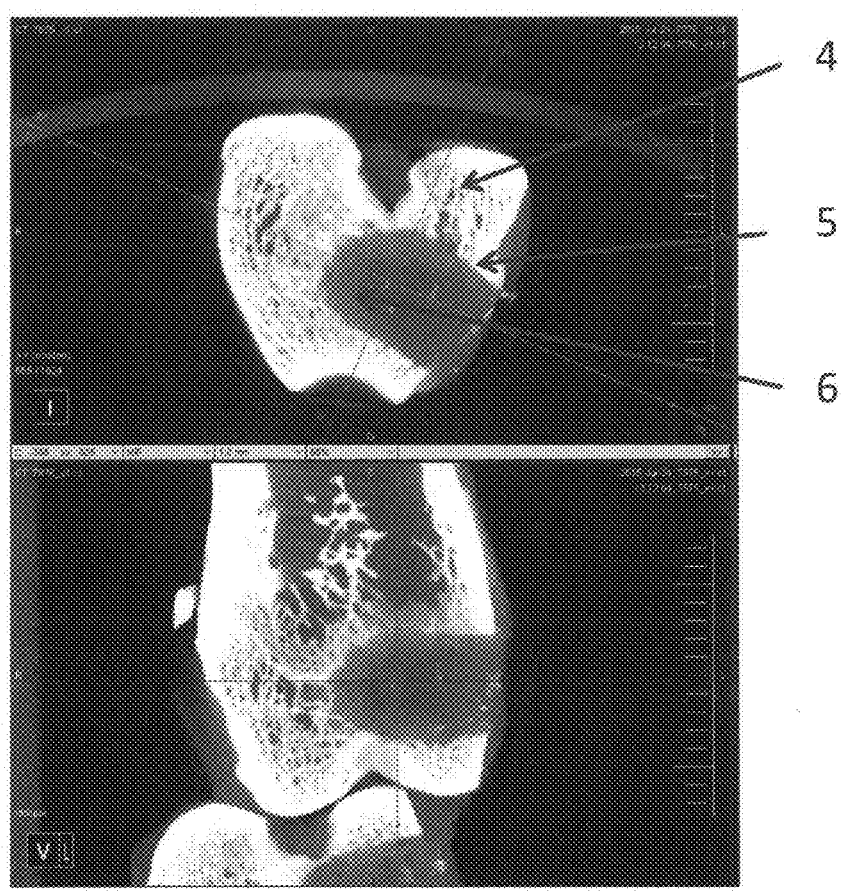
FIG. 2 is a microcomputed tomography image of the same defect as FIG. 1, according to embodiments of the present invention, in which (4) indicates the mineralization level of the surrounding, untreated bone, (5) indicates the margin of the defect, and (6) indicates the feint signal from the new woven bone.

Aspects of embodiments of the present invention are directed to enhancing bone formation and maturation by providing bone mineral donor species at the site where new bone formation is desirable, thus enhancing the process of bone mineralization or ossification. Furthermore, the kinetics of mineral release from the bone mineral donor species may be tailored to provide the minerals at the appropriate stages of new bone formation that occurs on the time scale of a few weeks to several months. This decrease in the length of time for new bone formation results in improved calcium and phosphate availability in mineralized bone grafts or synthetic grafts that complements the mineral demands due to the bone mineralization process. In some aspects, the mineralized forms of bone grafts lack the advantages of demineralized bone grafts in that they are not osteoinductive and are therefore slower to remodel into new bone. In the case of autografts and allografts, though osteoinductive bone morphogenic proteins (BMPs) are present they are 'masked' by the mineral composition of the graft, and thus are not able to be expressed in an appropriate manner to stimulate the response as assessed using various assay systems, particularly an in vivo model of intermuscular implantation. In the case of synthetic bone graft substitutes (e.g. hydroxyapatite (HA), tricalcium phosphate (TCP), and Bioglass (a silicate form of HA)) no BMPs are present and the overall bone formation response is limited. Furthermore, the kinetics of remodeling using synthetic bone graft substitutes is such that it is not well coupled to the natural bone formation process. TCP is generally considered to resorb too quickly, whereas HA and Bioglass resorb too slowly. This means that any mineral that is released from these materials is not well coupled to the demand of ossification.

Embodiments of the present invention encompass the mineral availability and ionic composition such that the right minerals are provided at the right time. Further, the inclusion of bone mineral donors provides radiopacity for radiographic visualization of the graft.

Definitions

"Healing" as used herein generally refers to the formation of tissue.

"Bioactive agent" is used herein to refer to therapeutic, prophylactic, and/or diagnostic agents. It includes without limitation physiologically or pharmacologically active substances that act locally or systemically in the body. "Bioactive agent" includes a single such agent and is also intended to include a plurality.

"Biocompatible" as generally used herein means the biological response to the material, device, or bone graft being appropriate for the intended application in vivo. Any metabolites of these materials should also be biocompatible.

"Blend" as generally used herein means a physical combination of different polymers, as opposed to a copolymer comprised of two or more different monomers.

"Controlled release" as generally used herein refers to time dependent release of bioactive agents such as calcium and phosphate ions. It generally refers to the sustained release of bioactive agents to prolong the therapeutic action of the bioactive agent, and preferably to maintain the concentration of the bioactive agent in a therapeutic window.

"Excipient" is a material that is added to a formulation to enhance physical handling characteristics rather than biological performance.

Extracellular matrix (ECM) as used herein describes a matrix or scaffold that provides a habitat for cellular population.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and absorbed or eliminated by the body within five years, whether degradation is due mainly to hydrolysis or mediated by metabolic processes.

As used herein, trace elements refer to elements that may be found naturally in bone, such as arsenic (Ar), copper (Cu), chromium (Cr), cobalt (Co), iron (Fe), fluoride (F), iodine (I), manganese (Mn), molybdenum (Mo), nickel (Ni), selenium (Se), silicon (Si), tin (Sn), vanadium (V), and zinc (Zn) as described in Jakob et al., 2010, "Nutritional Influences on Bone Health," pp. 81-86, the entire contents of which are herein incorporated by reference.

The popularity of demineralized bone matrix (DBM)-based products is based on the reported ability to induce bone formation through expression of inherent non-collagenous proteins that stimulate some cell types present at the graft site to differentiate into bone forming cells. This induction of bone formation process is referred to as "osteoinduction" and is due to the natural presence of bone morphogenic proteins (BMPs). DBM also provides a scaffold for these cells to populate and spread throughout in a process known as "osteoconduction." Demineralized bone in the form of a fiber, known as Demineralized Bone Fiber (DBF) has a physical form that has been shown to optimize and enhance the osteoconductive performance of DBM. In some embodiments of the present invention, a composition and method of manufacture of DBF fibers is as disclosed in U.S. Pat. Nos. 9,486,557 and 9,572,912, the entire contents of both of which are herein incorporated by reference. When DBM or DBF is combined with osteogenic cells which are capable of forming bone, the three mechanisms of bone healing (e.g., osteoinduction, osteoconduction, and osteogenesis) are combined.

Research to optimize bone healing has resulted in several advancements including attempts to enhance each of the processes. Recombinant technologies have been used to produce recombinant BMPs to enhance osteoinduction, while cell concentration and transplantation have been used to enhance osteogenesis and various matrices have been developed to enhance osteoconduction.

Aspects according to embodiments of the present invention enhance bone healing by providing appropriate minerals (calcium, phosphate, etc.) during the healing process to more rapidly generate completely mineralized new bone tissue. Calcium ions are toxic to cells above a certain level, and so, it is an aspect of this invention that the source of calcium ions is provided in a controlled release from a resorbable polymer fiber or particle.

During new bone formation, cells create a matrix known as osteoid, which is bone matrix, primarily type I collagen that has low mineral composition. The rapid formation of this new tissue exceeds the rate of bone mineral deposition such that it appears radiolucent with radiographic imaging and also lacks the structural properties that result from the formation of hydroxyapatite, i.e. bone mineral. The transformation of osteoid to mature bone occurs by a process known as ossification that results in a highly organized tissue that provides the structural properties required for skeletal support. However, aspects of embodiments of the current invention accelerate this process of ossification by providing the necessary mineral building blocks at the critical stage of rapid bone formation during the healing process by enriching the local environment appropriately and in a timely manner. Accordingly, while osteoblasts (immature bone cells) are laying down osteoid, in which they become encased and transition into osteocytes (mature bone cells), the enriched mineral composition of the healing milieu allows ossification to proceed in a more rapid fashion than for a composition that is not enriched with minerals.

Calcium homeostasis is tightly controlled by physiological mechanisms as it is used in multiple processes, not just for skeletal rigidity, including muscle contraction (skeletal and cardiac/smooth muscle). Too little calcium can impede these processes, whereas too much can result in problems such as plaque formation in arteries and heterotypic calcification in other tissues. As such, the normal concentration of calcium in extracellular fluids limits availability for the bone mineralization process. Another key material for bone formation is phosphate. Similar to calcium, phosphate has a relatively low concentration, and thus, is a limiting factor to bone mineralization.

Calcium and phosphate are combined during the process of ossification to form the primary bone mineral known as hydroxlyapatite. Hydroxylapatite, also commonly called hydroxyapatite (HA), is a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. Up to 50% by volume and 70% by weight of human bone is a modified form of hydroxyapatite (known as bone mineral).

By combining appropriate sources of bone minerals at the graft site where the demand is high bone healing may be accelerate by achieving complete remineralization of tissue faster thereby improving biomechanical integrity. DBF fibers are capable of facilitating the rapid production of new woven bone. The graft environment may be enhanced with appropriate mineral building blocks to support the next phase of the bone formation process and support complete remineralization and healing with greater biomechanical integrity at an earlier stage.

Simply adding calcium phosphate to a demineralized bone material such as DBF has been shown not to work (e.g., Example 3). It is important to provide a functioning material in order for controlled release of calcium ions to maintain the calcium ions at a safe and effective level. Accordingly, in some embodiments, the calcium and phosphate components are provided separately and also in a form that provide controlled delivery over the 2 to 8 week period in which enhancement of the rate of osteoid remineralization may be desired.

As disclosed herein, according to embodiments of the present invention, calcium compounds may be encapsulated in resorbable polymers to produce polymer fibers that provide a controlled release. Using DBF fibers allows for the use of demineralized bone in a form that maximizes the inductive and conductive components of the product to render a moldable putty form without the need for an excipient that may likely interfere with the healing process. The phosphate may be stored in the DBF by hydrating it in phosphate-buffered saline (PBS) and the calcium component may be stored in resorbable polymer fibers, rendering a product form that may be added to the DBF fibers without interfering with the handling characteristics, or masking the osteoinductive proteins.

Aspects of embodiments of the present invention provide a new strategy for enhancing bone formation and maturation by providing a bone graft matrix along with bone mineral donating species that provide requisite minerals for ossification and bone maturation during the key stages of this process, thereby accelerating the process such that structural integrity of the newly formed bone is achieved at earlier timepoints. Furthermore, the inclusion of bone mineral donor species provides a radiographic marker that allows for determination of bone graft placement which has particular utility for grafts such as demineralized bone matrix that are otherwise radiolucent, i.e. cannot be readily identified using radiographic imaging.

Compositions

Compositions and methods have been developed to produce bone graft devices that allow the release of bone minerals for enhancing new bone formation and maturation to enhance the rate and quality of new bone formation. In a preferred embodiment, the bone mineral donor species includes calcium and phosphate ions with release kinetics over a period from 1 week to 3 months.

In some embodiments of the invention, the calcium donor is encapsulated in a resorbable polymer to provide a controlled release. Calcium peroxide provides a material that will release calcium ions as it hydrates providing further control. The use of resorbable polymer fibers incorporated with calcium and or phosphate donor fibers with a sheath of a second resorbable polymer provides further control. An additional benefit of the use of the calcium and/or phosphate donor in a fiber form is that it can be easily mixed with demineralized bone matrix (e.g., DBF fibers) to provide the osteoinductive/osteoconductive component of the invention.

In some embodiments, the implants are temporary scaffolds that are incorporated into the body, and allow cell, tissue, and blood vessel in-growth as they resorb and remodel to appropriate tissue types, i.e. bone.

Scaffolds

In some embodiments, DBF is the form of scaffold for use in this invention and is an enhanced form of DBM. The popularity of DBM-based products is based on the reported ability to induce bone formation through expression of inherent non-collagenous proteins that stimulate some cell types present at the graft site to differentiate into bone forming cells. This process has been termed 'osteoinduction' and is due to the natural presence of bone morphogenetic proteins (BMPs). DBM also provides a scaffold for these cells to populate and spread throughout in a process known as osteoconduction. Demineralized bone in the form of a fiber, known as DBF (Demineralized Bone Fiber) has a physical form that has been shown to optimize and enhance the osteoconductive performance of DBM, as disclosed in US Patent Publication No. 2014/0314822. When DBM or DBF is combined with cells capable of forming bone by osteogenesis, the 3 mechanisms of bone healing can be combined.

The fibers may vary in their dimensions such as length, width and thickness according to the intended applications. The ability to control these parameters with precision allows for the possibility of tissue-engineered constructs. The use of the controlled geometry particles to make e range of forms is contemplated in the present invention.

The process according to embodiments of the present invention forms an elongated fiber particle having a length from about 1 cm to about 30 cm. In some embodiments, an elongated fiber particle of the present invention has a length from about 3 cm to about 18 cm. In other embodiments, an elongated fiber particle of the present invention has a length from about 3 cm to about 10 cm. In still other embodiments, an elongated fiber particle of the present invention has a length from about 4 cm to about 8 cm.

The process according to embodiments of the present invention forms an elongated fiber particle having a width from about 0.05 mm to about 4 mm. In some embodiments, an elongated fiber particle of the present invention has a width from about 0.2 mm to about 1 mm. In other embodiments, an elongated fiber particle of the present invention has a width from about 0.5 mm to about 1 mm.

The process according to embodiments of the present invention forms an elongated fiber particle having a thickness from about 0.05 mm to about 4 mm. In some embodiments, an elongated fiber particle of the present invention has a thickness from about 0.2 mm to about 1 mm. In other embodiments, an elongated fiber particle of the present invention has a thickness from about 0.5 mm to about 1 mm.

Research to optimize bone healing has resulted in several advancements including attempts to enhance each of the three mechanisms of this process. Recombinant technologies have been used to produce recombinant BMPs to enhance osteoinduction, cell concentration and transplantation have been used to enhance osteogenesis and various matrices have been developed to enhance osteoconduction.

During new bone formation cells create a matrix known as osteoid, which is bone matrix, primarily type I collagen that has low mineral composition. The rapid formation of this new tissue exceeds the rate of bone mineral deposition such that it appears radiolucent with radiographic imaging and also lacks the structural properties that result from the formation of hydroxyapatite, i.e. bone mineral. The transformation of osteoid to mature bone occurs by a process known as ossification that results in a highly organized tissue that provides the structural properties required for skeletal support. The current invention accelerates this process of ossification by providing the necessary mineral building blocks at the critical stage of rapid bone formation during the healing process by enriching the local environment appropriately and timely. So while osteoblasts (immature bone cells) are laying down osteoid, in which they become encased and transition into osteocytes (mature bone cells), the enriched mineral composition of the healing milieu allows ossification to proceed in a more rapid fashion than in the milieu that naturally occurs.

In some embodiments, the source of tissue for scaffold is allogeneic, i.e. of the same species, so human for human use, canine for canine use etc. In some embodiments, xenogeneic material may also be used.

Other scaffolds including non-demineralized allograft or xenograft including particulate cortical and/or cancellous bone. Furthermore, non-biologically derived scaffold material such as synthetic polymer fibers could be used. In some embodiments, the synthetic polymer fibers contain an osteoinductive material such as bone morphogenetic proteins (BMPs).

Bioactive Agents

DBM and DBF are bioactive agents due to the natural presence of BMPs. This is demonstrated experimentally by placing them into non-boney sites (heterotopic) such as intermuscular pouches as used in the intermuscular osteoinductive assay.

In addition to these naturally occurring growth and differentiating factors, it is appreciated that exogenous agents such as recombinant BMPs may be added to further enhance performance of the current invention. As these agents stimulate a robust bone formation response the need for bone mineral donors is also present and will enhance the maturation of the new osteoid to load bearing bone.

In addition to the calcium ion donor described below, the composition may provide other beneficial agents by use of calcium peroxide that will also deliver oxygen to the graft site, or calcium ascorbate that will provide an anti-oxidant source to counter any reactive oxygen species in the graft site.

Calcium (and/or Phosphate) Donor Materials

In order to control the availability of the bone mineral ions, the donor material is formed within a resorbable polymer fiber or particulate.

Resorbable polymers are biocompatible polymers capable of resorbing in the body and have a physical strength to form a fiber or particle at room temperature. Non-limiting examples of resorbable polymers for use with a calcium or phosphate donor material that may be used to prepare the controlled release materials include, proteins, including silk, collagen (including Types I to V and mixtures thereof), and proteins comprising one or more of the following amino acids: alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine; polysaccharides, including alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan; resorbable polyesters, including resorbable polyesters made from hydroxy acids (including resorbable polyesters like poly(lactides), poly(glycolides), poly(lactide-co-glycolides), poly(lactic acid), poly(glycolic acid), poly (lactic acid-co-glycolic acid), poly(dioxanones), polycaprolactones and polyesters with one or more of the following monomeric units: glycolic, lactic; trimethylene carbonate, p-dioxanone, or ε-caprolactone, and resorbable polyesters made from diols and diacids; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); biocompatible copolymers (including block copolymers or random copolymers); and hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone or combinations thereof. Resorbable polymers of the present invention also include cross-linked polymers, and include, for example, cross-linked collagen, as well as functionalized polymers. In some embodiments, resorbable polymers are resorbable polyesters.

In some embodiments, the calcium donor includes salts such as calcium peroxide, calcium ascorbate, calcium sulfate, calcium phosphate, calcium carbonate, calcium chloride, or mixtures thereof. In some embodiments of the present invention, the calcium donor is calcium peroxide. Additionally, as calcium peroxide reacts, oxygen is released to the graft site.

Trace elements such as silicon and magnesium have also been found to enhance bone formation. Other essential trace elements include arsenic (Ar), copper (Cu), chromium (Cr), cobalt (Co), iron (Fe), fluoride (F), iodine (I), manganese (Mn), molybdenum (Mo), nickel (Ni), selenium (Se), silicon (Si), tin (Sn), vanadium (V), and zinc (Zn). In some embodiments of the present invention, any one or more of the essential trace elements (e.g., silicon and/or magnesium) may be included in the controlled release formulations.

It may be desirable to affect control of the pH around the implant. In some embodiments of the present invention, incorporating buffer components (e.g., PBS or components of PBS) into the formulation may maintain the desired pH.

Bone Healing Devices and Methods of Manufacturing

Methods have been developed to produce bone graft devices that allow the release of bone minerals for bone maturation along with scaffolds for supporting the new bone formation.

Demineralized Bone Matrix (DBM) and Demineralized Bone Fibers (DBF)

The osteoinductive and osteoconductive portion of the composition of the invention is formed from demineralized bone matrix (DBM). For example, the demineralized bone matrix may be in a fiber format (DBF) or may be formed in a particulate format. DBM may be manufactured by any of the methods known in the art, including pulverizing cortical bone or otherwise forming a powder with sizes ranging from about 50-about 750 microns in diameter that are then demineralized by placing the powder into an acid such as hydrochloric acid. In some embodiments, fibers may be manufactured from demineralized cortical bone using, for example, the methods disclosed in US Patent Publication No. 2014/0314822, the entire contents of which is herein incorporated by reference.

Briefly, the bone is cut into struts that are then placed in dilute acid to effect demineralization. The demineralized cortical struts are then cut or shaved using a blade to form ribbon like fibers, that may be up to 4 cm or greater in length. Fibers that are 0.1 to 1.5 mm wide and 0.05 to 0.5 mm thick allow for appropriate surface area and flexibility so they are readily entangled into a coherent mass. It is recognized that the length and aspect ratios of the DBF may be optimized depending on defect size, i.e. small periodontal defects are better treated with small fibers (shorter and more thread-like) whereas larger defects requiring larger volumes require larger size fibers. The bone may be derived from allogeneic or xenogeneic sources. For human applications, human bone is considered allogeneic. For veterinary applications in various species (e.g., canine, feline, equine as examples), bone from the same species would be considered allogeneic.

DBF has handling characteristics that allow them to be used without further formulation in a bone graft. For DBM powder, an excipient such as polyoxamer is required to render the material suitable for handling. Other non-limiting examples of suitable excipients include: glycerol, lecithin, hyaluronic acid, alginate, derivatized hyaluronic acids, and modified celluloses including carboxyl methyl cellulose and hydroxypropyl cellulose.

Optionally, in some embodiments, the fibers may be dried and then rehydrated in a glycerol solution and further dried by lyophilization or vacuum afterward. Excipients allow for modification of the handling properties, including rehydration, of the material for ease of use in surgical applications, but are not required.

Optionally, in some embodiments, the DBF fibers or DBM particulates may be dried and then rehydrated in a phosphate buffered saline (PBS) or other phosphate solution and further dried by lyophilization or vacuum afterward to provide a DBM particulate or DBF that acts as a source of phosphate ions.

Calcium (and/or Phosphate) Donor Materials

In order to control the availability of the bone mineral ions, the donor material is formed within a resorbable polymer fiber or particle. Resorbable polymer fibers may be produced using melt, electro, or a wet spinning technique Various processes can be used to produce fibers including melt, electro and wet spinning. Resorbable polymers such as polycaprolactone (PCL), Polylactic acid (PLA), or Poly (lactic co-glycolic acid) may be formed into solution in, for example, chloroform. Using a syringe pump and stainless steel Luer-Lok® needle the polymer solution, with added bone mineral ion donor, such as calcium peroxide is precipitated into a non-solvent such as methanol. The resultant fibers may be collected and dried. These fibers when placed in water will degrade liberating calcium and oxygen over a sustained period. Control over degradation rate may be varied by using different polymers, and also by using a coaxial needle that allows a sheath polymer to be produced allowing a bicomponent fiber with greater potential for parameter control. Selection of solvent/non solvent pairs will depend on the polymer being used and the examples above are non-limiting.

In still a further embodiment, the bone mineral ion donor particulate may be in the form of or may contain spheres, including micro- and nano-spheres that encapsulate calcium salts. These spheres or particles may be produced, for example, by emulsion-solvent evaporation, evaporation/extraction, phase separation/coacervation, self-assembly, solvent displacement, rapid expansion of supercritical solutions, spray drying or microfluidization.

The bone mineral donor and DBF material has utility as a bone graft without further modification; however, in some embodiments, 'procedure specific' forms may have added utility, and these can be produced by various methods similar to those used for non-woven textiles, as described in US Patent Publication No. 2014/0314822. Wet laying is one such method. This allows for forming the DBF with incorporated bone mineral donors materials into coherent 3-D shapes such as strips, cones, spheres, etc. In forming the 3-D shapes, the bone mineral ion donor species can readily be incorporated and controlled to provide the desired controlled release of the bone mineral ions.

IV Methods of Using the Enhanced Bone Grafts with Calcium Donor Species

The devices are intended to be used as bone grafts for a broad range of indications where new bone formation is desirable. The largest indication is for spinal fusions including interbody fusions in the intervertebral disc space, posterolateral fusions and scoliosis for deformity correction. Other defects of the skeleton include those caused by trauma, bone cysts and other defects. In addition, oral maxillofacial indications are common, for example periodontal defects where the loss of teeth creates voids and bone loss that needs to be rebuilt prior to restorative dental implant placement. Edentulous jaw bones tend to narrow where bone that does not undergo loading is resorbed—according to Wolff's law stating that bone is stimulated, strengthened, and renewed directly by a tooth or an implant. The same holds for situations where normal physiological loading is absent such as in bed ridden patients and in jaw bones with no teeth. In this indication, augmentation of the alveolar ridge is required to provide a solid foundation for implants. Typically, the site is bone grafted and allowed to heal prior to implant placement, such that this is a two-stage procedure. The decision for when to place the implants is made once radiographic evidence of new bone is determined. The ability of the enhanced bone graft (DBF+bone mineral donor) to establish new mature bone that is radiopaque more rapidly allows earlier implant placement and dental reconstruction, allowing the patient to return to normal daily activities such as chewing food.

The following Examples are presented for illustrative purposes only, and do not limit the scope or content of the present application.

Example 1

Struts of rabbit bone weighing 300 grams were placed in 3000 ml of 0.6 M hydrochloric acid for 6 days, with the acid changed every day. After this time, the struts were demineralized, as could be confirmed by the ability to bend them by hand. They were rinsed in buffer and stored in a freezer until the next step in the process. A blade with openings 0.030"×0.050" and a tooth height of 0.012" was used to produce fibers. The fibers were placed in phosphate buffer (e.g., PBS) for 45 minutes.

Fibers were blotted to remove excess buffer and 1 gram placed in jars and foil pouches. Thereafter, the product was sterilized using electron beam sterilization.

The fibers were hydrated and formed a "putty" that could be utilized as a bone graft.

Example 2

To 5 grams of the material of Example 1, 5 grams of particulate TCP (Berkeley Biomaterials Inc. Bio G Raw) was added and mixed to provide an even dispersion. The resultant mixture was dried in a vacuum oven.

Example 3

Material from Example 2 was placed into an intermuscular pouch model in an athymic rat, and the healing process evaluated. In a second experimental group, DBF alone from Example 1 was used. The implant size was 200 microliters.

DBF was found to be osteoinductive at 6 weeks. There were areas where bone formation via endochondral ossification was evident, i.e. areas of round plump chondrocytes preceding the calcification of the collagen matrix into new bone. Areas of bone marrow are abundant in most implants indicating mature new bone. No immune response was seen due to the presence of DBF in this study.

TCP containing implants (i.e., bone grafts) did not perform well. No new bone formation was seen in the implants where TCP was present.

Example 4

A polycaprolactone (PCL) in chloroform solution was prepared adding 4.5 g of polycaprolactone to 30 ml of chloroform. 0.47 grams of calcium peroxide was added to 8.56 grams of the polymer solution and loaded into a 10 ml glass syringe fitted with an 18 gauge Luer-Lok® stainless steel needle. The solution was precipitated into methanol at a rate of 0.5 ml/min to yield a fiber. The fiber was collected and dried in a vacuum oven.

Example 5

0.5 grams of Calcium Phosphate was added to 16 grams of the polycaprolactone (PCL) solution of example 4 and the mixture placed into a 10 ml glass syringe. Using a syringe pump and 18 gauge needle, the solution was precipitated into methanol at a rate of 0.5 ml/min to yield a fiber. The fiber was collected and dried in a vacuum oven.

Example 6

A solution of 3 grams of polylactic acid (PLA) in 30 ml of chloroform was prepared. 0.5 grams of calcium peroxide was added to 7.5 grams of the polymer solution and loaded into a 10 ml glass syringe fitted with an 18 gauge Luer-Lok® stainless steel needle. The solution was precipitated into methanol at a rate of 0.5 ml/min to yield a fiber. The fiber was collected and dried in a vacuum oven.

Example 7

A solution of 3 grams of polylactic acid (PLA) in 30 ml of chloroform was prepared. 0.5 grams of calcium peroxide was added to 7.5 grams of the polymer solution and loaded into a 10 ml glass syringe. 10 grams of the PLA solution was placed in a second 10 ml glass syringe. The two syringes were connected to a coaxial needle (Rame-Hart) with the calcium peroxide containing component forming the inner part of the fiber. The solution was precipitated into methanol at a rate of 0.5 ml/min to yield a fiber with a ratio of 4:1 for outer to inner volume. The fiber was collected and dried in a vacuum oven.

Example 8

1 gram of fiber from Example 1 was added to 1 gram of fiber from Example 6 and mixed. The resultant material was then placed in a vacuum oven to dry the DBF fiber.

Example 9

1 gram of fiber from example 1 was added 1 gram of fiber from example 5 and mixed. The resultant material was then placed in a vacuum oven to dry the DBF fiber.

Example 10

Figure 3:
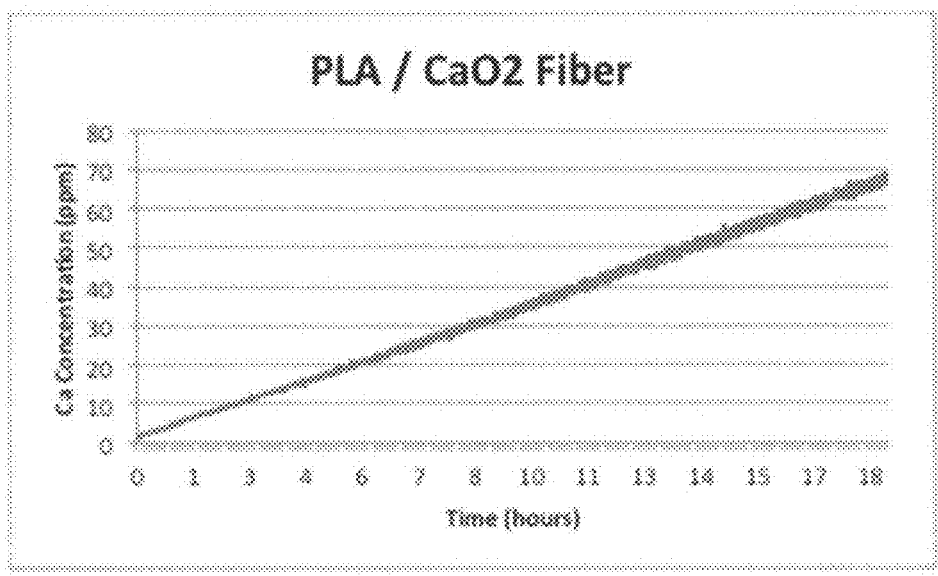
FIG. 3 is a graphical representation of calcium ion release from a poly lactic acid (PLA) encapsulated calcium peroxide (CaO2), according to embodiments of the present invention.

Calcium ion release was measured from a 0.236 gram sample of fiber from example 7 placed into 100 ml of water. Measurements were made using a Cole Parmer ion selective electrode connected to an Oakton Meter with data logging capability. The baseline calcium concentration was 1 ppm. This increased to 2.8 ppm at 20 minutes, 4.28 ppm at 43 minutes and 66 ppm at 18 hours. The release data are shown graphically in FIG. 3.

Example 11

Calcium ion release was measured from a 0.230 gram sample of fiber from example 6 placed into 100 ml of water.

Figure 4:
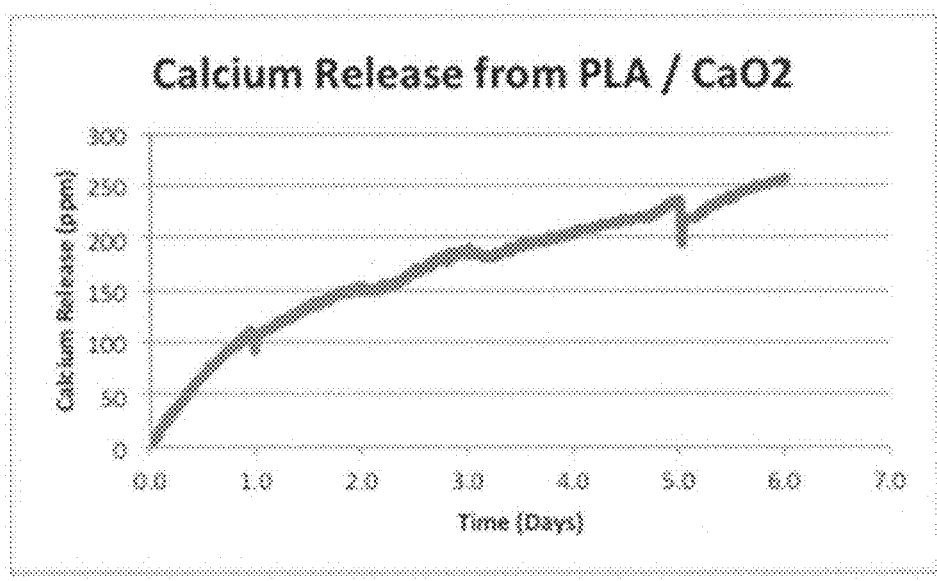
FIG. 4 is a graphical representation of calcium ion release from a poly lactic acid (PLA) encapsulated calcium peroxide (CaO2), according to embodiments of the present invention.

The baseline calcium concentration was 1 ppm. and increased to 260 ppm after 6 days. The release data are shown graphically in FIG. 4.

Example 12

Figure 5:
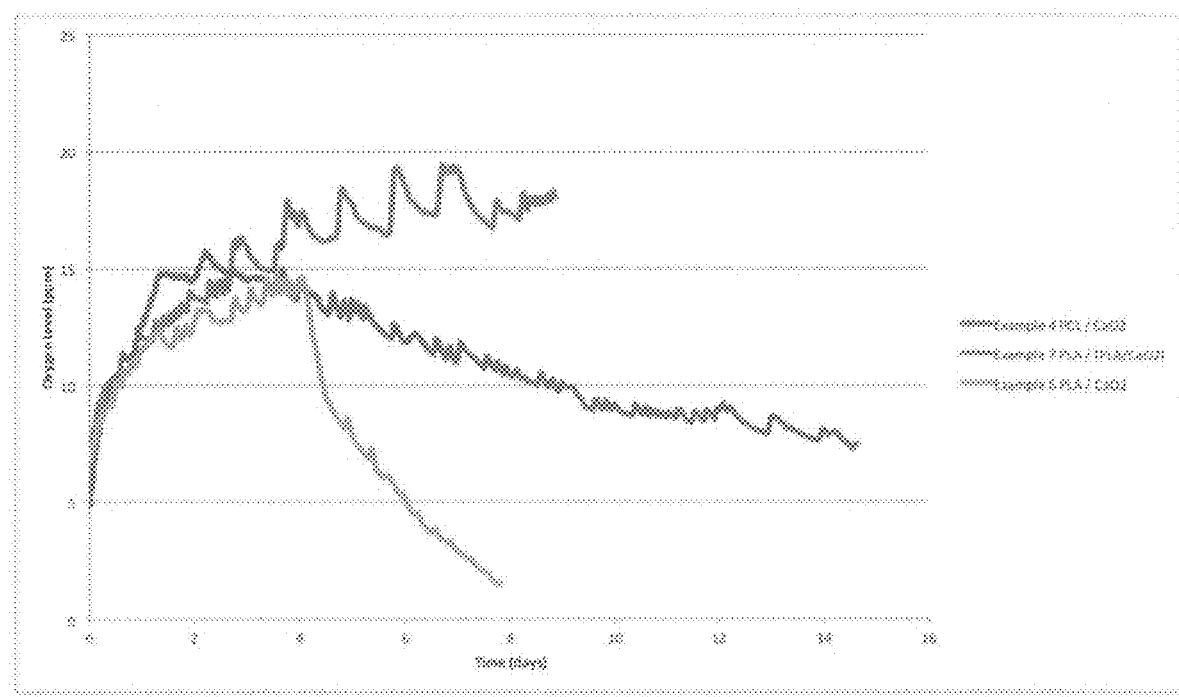
FIG. 5 is a graphical representation of oxygen release from fibers of: calcium peroxide (CaO2) encapsulated in polylactic acid (PLA) (Example 6 shown in green); calcium peroxide (CaO2) encapsulated in and polycaprolactone (PCL) (Example 4 shown in blue), and a core-sheath fiber wherein a polylactic acid (PLA)/calcium peroxide (CaO2) fiber has an outer sheath of polylactic acid (PLA) (Example 7 shown in red, according to embodiments of the present invention.

Oxygen release was measured from a 0.100 gram sample of fiber from examples 4, 6 and 7 placed into 40 ml of water. The measurements were made using a PreSens MicrOx needle type oxygen microsensor. The release data are shown graphically in FIG. 5. Note the drop in oxygen level shown in the traces from fiber from Examples 6 and 7 is due to leakage of oxygen from the measurement system. The oxygen release from fiber from Example 4 is still increasing demonstrating that the rate of evolution of oxygen from the fiber is outpacing leakage from the measurement system.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A demineralized bone matrix (DBM) fiber scaffold having controlled release calcium ions, the DBM fiber scaffold consisting of:
   a resorbable polymer fiber incorporated with a calcium ion donor to form a calcium-incorporated resorbable polymer fiber, the calcium-incorporated resorbable polymer fiber having an outer polymer sheath;
   demineralized bone matrix (DBM) fibers mixed with the calcium-incorporated resorbable polymer fiber;
   magnesium and/or silicon; and
   a phosphate-containing buffer;
   wherein the calcium ion donor is calcium peroxide, calcium ascorbate, calcium sulfate, calcium phosphate, calcium carbonate, calcium chloride, and mixtures thereof; and
   wherein the DBM fibers have a length from about 1 cm to about 30 cm, a width from about 0.05 mm to about 4 mm, and a thickness from about 0.05 mm to about 4 mm.

2. The DBM fiber scaffold of claim 1, wherein the DBM fiber scaffold is in the form of a strip, a sphere, a cylinder, or a cone.

3. The DBM fiber scaffold of claim 1, wherein the resorbable polymer fibers are selected from the group consisting of proteins, peptides, silk, collagen, polysaccharides, resorbable polyesters, including resorbable polyesters made from hydroxy acids, resorbable polyesters made from diols and diacids; polycarbonates; tyrosine polycarbonates, natural and synthetic polyamides, natural and synthetic polypeptides, natural and synthetic polyaminoacids, polyesteramides, poly(alkylene alkylates), polyethers, polyvinyl pyrrolidones, polyurethanes, polyetheresters, polyacetals, polycyanoacrylates, poly(oxyethylene)/poly(oxypropylene) copolymers, polyacetals, polyketals, polyphosphates, (phosphorous-containing) polymers, polyphosphoesters, polyalkylene oxalates, polyalkylene succinates, poly(maleic acids), biocompatible copolymers, hydrophilic or water soluble polymers, and combinations thereof.

4. The DBM fiber scaffold of claim 3, wherein:
   the collagen is selected from the group consisting of Types I, II, III, IV, V and combinations thereof;
   the proteins or peptides comprise one or more of alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine;
   the polysaccharides are selected from alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan;
   the resorbable polyesters are selected from the group consisting of poly(lactides), poly(glycolides), poly(lactide-co-glycolides), poly(lactic acid), poly(glycolic acid), poly(lactic acid-co-glycolic acid), poly(dioxanones), polycaprolactones and polyesters with one or more of the following monomeric units: glycolic, lactic; trimethylene carbonate, p-dioxanone, or ε-caprolactone;
   the polyethers are selected from polyethylene glycol (PEG) or polyethylene oxide (PEO); and
   the biocompatible copolymers are selected from the group consisting of polyethylene (PEG) or (PVP) with a block of a different biocompatible or biodegradable polymers selected from the group consisting of poly(lactide), poly(lactide-co-glycolide), polycaprolactone and combinations thereof.

5. A demineralized bone matrix (DBM) fiber scaffold having controlled release calcium ions, the DBM fiber scaffold consisting of:
   a resorbable polymer fiber incorporated with a calcium ion donor to form a calcium-incorporated resorbable polymer fiber, the calcium-incorporated resorbable polymer fiber having an outer polymer sheath;
   demineralized bone matrix (DBM) fibers mixed with the calcium-incorporated resorbable polymer fiber;
   magnesium and/or silicon;
   a phosphate-containing buffer; and
   an excipient selected from the group consisting of glycerols, lecithins, polyoxamers, surfactants, and phospholipids;
   wherein the calcium ion donor is calcium peroxide, calcium ascorbate, calcium sulfate, calcium phosphate, calcium carbonate, calcium chloride, and mixtures thereof; and
   wherein the DBM fibers have a length from about 1 cm to about 30 cm, a width from about 0.05 mm to about 4 mm, and a thickness from about 0.05 mm to about 4 mm.

6. A method of repairing a bone or a bone defect in a subject in need thereof, comprising implanting the DBM fiber scaffold of claim 1.

* * * * *